United States Patent
Borenstein et al.

(10) Patent No.: US 11,015,161 B2
(45) Date of Patent: May 25, 2021

(54) ELECTROPORATION AIDED BIOLOGICAL MATERIAL DELIVERY SYSTEM AND METHOD

(71) Applicant: The Charles Stark Draper Laboratory, Inc., Cambridge, MA (US)

(72) Inventors: Jeffrey T. Borenstein, Newton, MA (US); Jenna L. Balestrini, Boston, MA (US); Vishal Tandon, Roxbury Crossing, MA (US); Louis B. Kratchman, Quincy, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 167 days.

(21) Appl. No.: 16/123,539

(22) Filed: Sep. 6, 2018

(65) Prior Publication Data
US 2019/0071628 A1    Mar. 7, 2019

Related U.S. Application Data

(60) Provisional application No. 62/554,781, filed on Sep. 6, 2017.

(51) Int. Cl.
*B01L 3/00* (2006.01)
*C12M 3/00* (2006.01)
(Continued)

(52) U.S. Cl.
CPC ....... *C12M 35/02* (2013.01); *B01L 3/502753* (2013.01); *C12M 23/16* (2013.01);
(Continued)

(58) Field of Classification Search
CPC .............................. C12M 35/00; C12M 35/02
See application file for complete search history.

(56) References Cited

U.S. PATENT DOCUMENTS 5,585,069 A * 12/1996 Zanzucchi ........... B01J 19/0093
422/505
6,846,668 B1 * 1/2005 Garman ................. C12M 35/00
435/285.1
(Continued)

FOREIGN PATENT DOCUMENTS

JP    2012034641 A    2/2012
WO   2006112870 A1   10/2006
(Continued)

OTHER PUBLICATIONS

International Search Report and Written Opinion dated Apr. 13, 2018 in PCT Application No. PCT/US2017/067998.
(Continued)

*Primary Examiner* — Nathan A Bowers
(74) *Attorney, Agent, or Firm* — McDermott Will & Emery LLP

(57) ABSTRACT

Microfluidic devices and associated methods are disclosed. A microfluidic device includes a target entrainment channel and an effluent channel on opposing sides of a semipermeable membrane. A restrictor channel that is narrower than the effluent channel is interposed between the semipermeable membrane and the effluent channel. Fluid that flows from the target entrainment channel, through the semipermeable membrane and the restrictor channel to the effluent channel, pins target cells along the center of the target entrainment channel for electroporation using an electrode in the channel.

12 Claims, 16 Drawing Sheets

(51) Int. Cl.
*C12M 1/42* (2006.01)
*C12N 15/87* (2006.01)
*C12N 13/00* (2006.01)
*C12M 1/12* (2006.01)
*C12M 3/06* (2006.01)

(52) U.S. Cl.
CPC ............. *C12M 25/02* (2013.01); *C12N 13/00* (2013.01); *C12N 15/87* (2013.01); *B01L 2200/0668* (2013.01); *B01L 2200/12* (2013.01); *B01L 2300/0645* (2013.01); *B01L 2300/0681* (2013.01); *B01L 2300/0887* (2013.01)

(56) References Cited

U.S. PATENT DOCUMENTS

| | | | | |
|---|---|---|---|---|
| 8,173,415 | B2* | 5/2012 | Noori | C12M 1/00 435/285.1 |
| 2002/0137121 | A1 | 9/2002 | Rubinsky et al. | |
| 2002/0182627 | A1* | 12/2002 | Wang | G01N 33/5005 435/6.11 |
| 2003/0148524 | A1 | 8/2003 | Zimmermann et al. | |
| 2007/0048857 | A1* | 3/2007 | Ito | B01L 3/5085 435/283.1 |
| 2007/0155016 | A1* | 7/2007 | Lee | B01L 3/502707 435/461 |
| 2008/0081372 | A1 | 4/2008 | Huang | |
| 2009/0098541 | A1* | 4/2009 | Southern | C12Q 1/6876 435/6.11 |
| 2010/0263599 | A1* | 10/2010 | Yanik | G01N 33/5082 119/216 |
| 2014/0378352 | A1* | 12/2014 | Daridon | C12M 1/34 506/39 |
| 2016/0338347 | A1 | 11/2016 | White et al. | |

FOREIGN PATENT DOCUMENTS

| | | |
|---|---|---|
| WO | 2009123564 A1 | 10/2009 |
| WO | 2017106727 A1 | 6/2017 |

OTHER PUBLICATIONS

Adamo, Andrea, et al. "Flow-through comb electroporation device for delivery of macromolecules" Anal Chem., vol. 85, No. 3, pp. 1637-1641, Feb. 5, 2013.

Chang, Lingqian, et al. "Dielectrophoresis-assisted 3D nanoelectroporation for non-viral cell transfection in adoptive immunotherapy" Royal Society of Chemistry, Lab on a Chip, vol. 15, Jun. 2015.

Chang, Lingqian, et al. "Micro-/nanoscale electroporation" Royal Society of Chemistry, Lab on a Chip, vol. 16, Sep. 2016.

Geng, Tao, et al. "Microfluidic electroporation for cellular analysis and delivery" Royal Society of Chemistry, Lab on a Chip, vol. 13, Jul. 2013.

Zhu, Tao, et al. "Electroporation based on hydrodynamic focusing of microfluidics with low dc voltage" Biomed Microdevices, vol. 12, pp. 35-40, Sep. 2010.

Invitation to Pay Additional Fees and, Where Applicable, Protest Fee dated Nov. 29, 2018 in PCT Application No. PCT/US2018/049704.

International Search Report and Written Opinion dated Jan. 23, 2019 in PCT Application No. PCT/US2018/049704.

Diaz, R, et al. "A single cell study on the temperature effects of electroporation" In ASME 2004 International Mechanical Engineering Congress and Exposition, Nov. 13-20, 2004, 7 pages.

Office Action dated Mar. 18, 2019 in U.S. Appl. No. 15/851,393.

* cited by examiner

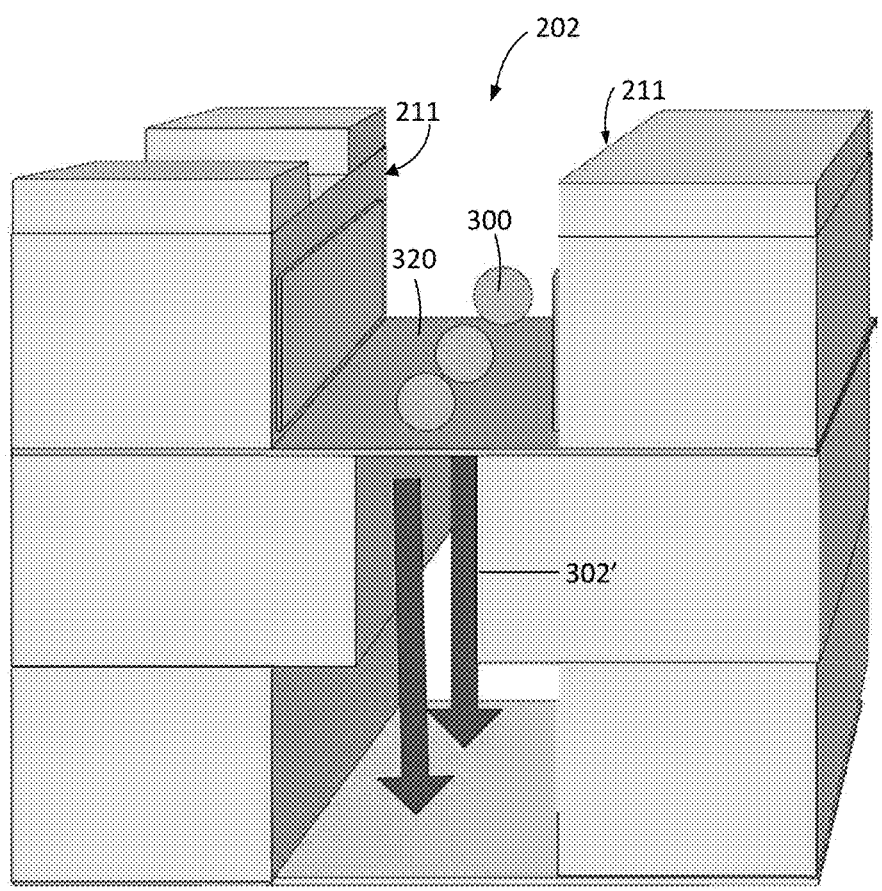
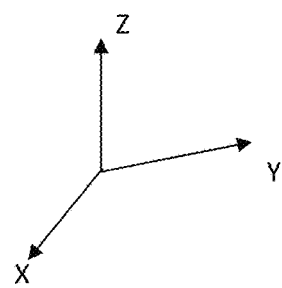
FIG. 3C

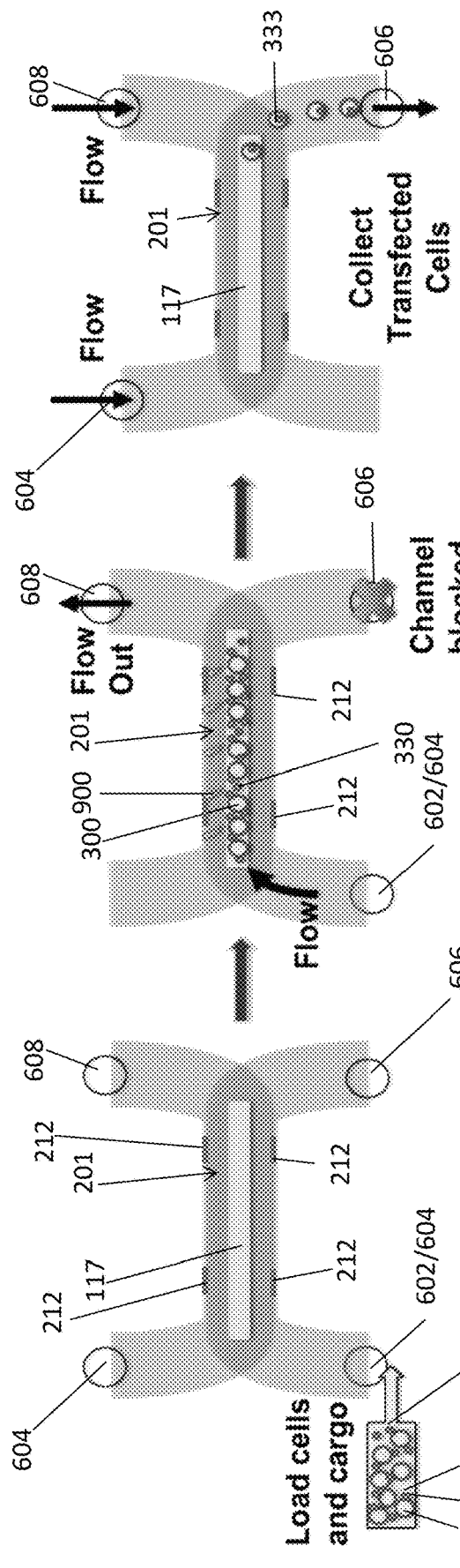

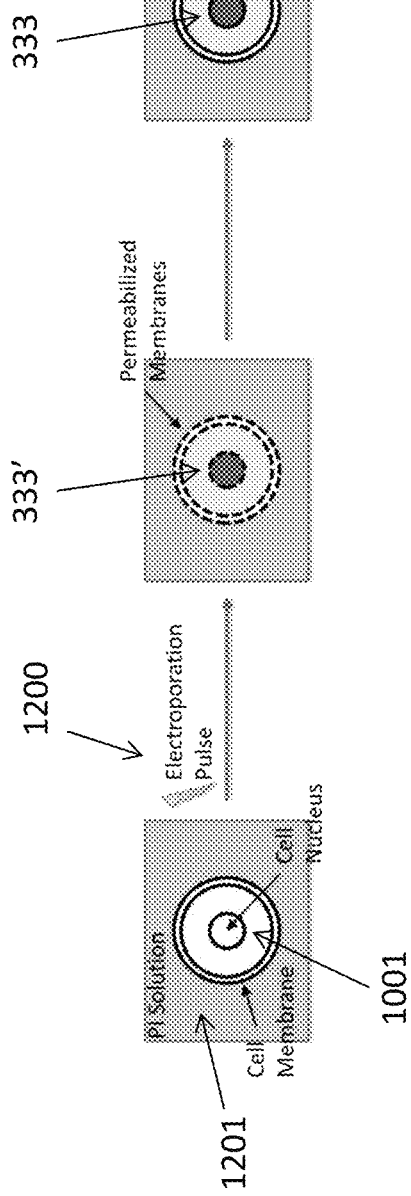
FIG. 12A
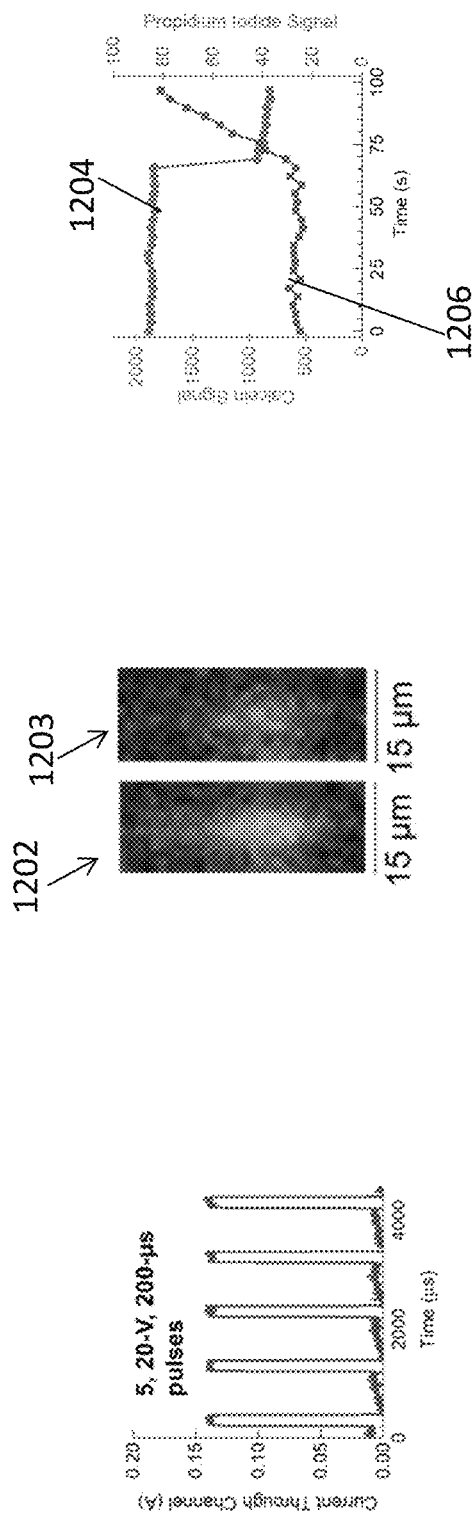
FIG. 12D
FIG. 12C
FIG. 12B

ELECTROPORATION AIDED BIOLOGICAL MATERIAL DELIVERY SYSTEM AND METHOD

CROSS-REFERENCE TO RELATED APPLICATIONS

The present application claims the benefit of, and priority to, U.S. Provisional Patent Application No. 62/554,781, titled "ELECTROPORATION AIDED BIOLOGICAL MATERIAL DELIVERY SYSTEM AND METHOD" and filed on Sep. 6, 2017, which is hereby incorporated by reference herein in its entirety.

BACKGROUND

Various treatments for a variety of medical conditions involve the transfer of exogenous genetic information into cells of a patient or a cell donor. For example, CAR-T (chimeric antigen receptor T cell) technology involves taking blood samples from a patient and processing those cells in a manner that returns genetically engineered populations of T cells to the patient's body once they have been programmed to recognize specific antigens on targeted cells. Typically, genes are transferred into T cells by viral transduction with a retrovirus (e.g., lentivirus), but they can also be transfected into cells using physical methods such as electroporation or cell constriction within channels, chemical methods, or other approaches.

SUMMARY OF THE DISCLOSURE

According to one aspect of the disclosure, a microfluidic device is provided that includes a first substrate having a first side, an opposing second side, and a first channel. The microfluidic device also includes an electrode operable to generate an electric field in the first channel. The microfluidic device also includes a semipermeable membrane having a first side that is attached to the opposing second side of the first substrate and that spans the first channel. The microfluidic device also includes a second substrate attached to an opposing second side of the semipermeable membrane and having a second channel adjacent the semipermeable membrane and a third channel fluidly coupled to the second channel. The first channel, the second channel, and the third channel each have an elongate dimension parallel to the semipermeable membrane. The third channel is relatively wider than the second channel in a direction parallel to the semipermeable membrane and perpendicular to the elongate dimensions of the first, second, and third channels.

According to another aspect of the disclosure, a method is provided that includes flowing target cells, cargo elements, and a fluid from a target introduction channel into a target entrainment channel. The method also includes passing at least a portion of the fluid through a semipermeable membrane that spans the target entrainment channel. The method also includes preventing, with the semipermeable membrane, the target cells and potentially also the cargo elements from passing through the semipermeable membrane. The method also includes flowing the at least the portion of the fluid that has passed through the semipermeable membrane through a restrictor channel to an effluent channel. The effluent channel has a width that is larger than a width of the restrictor channel. The method also includes holding the target cells against a first side of the semipermeable membrane in the target entrainment channel with the at least the portion of the fluid passing through the semipermeable membrane. The method also includes activating at least one electrode in the target entrainment channel while holding the target cells against the first side of the semipermeable membrane in the target entrainment channel. The method also includes electroporating the target cells that are held against the first side of the semipermeable membrane within the target entrainment channel with an electric field generated by the activated at least one electrode. The method also includes passing at least one cargo element into at least one of the electroporated target cells.

According to another aspect of the disclosure, a method is provided that includes providing a first substrate having a first side, an opposing second side, and a first channel that extends from the first side to the opposing second side. The method also includes forming an electrode on a sidewall of the first channel. The method also includes providing a second substrate having a second channel and a third channel, wherein the third channel is relatively wider than the second channel. The method also includes providing a semipermeable membrane. The method also includes attaching a first side of the semipermeable membrane to the opposing second side of the second substrate. The method also includes attaching the second substrate to an opposing second side of the semipermeable membrane such that the first channel, the second channel, and the third channel each have a coaligned elongate dimension that is parallel to the semipermeable membrane. The third channel is relatively wider than the second channel in a direction parallel to the semipermeable membrane and perpendicular to the coaligned elongate dimensions of the first, second, and third channels when the first substrate and the second substrate are attached to the semipermeable membrane.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 3A-3E illustrate various stages of operation of the microfluidic device shown in FIG. 2 in accordance with various aspects of the subject disclosure.

FIGS. 9A-9C illustrate various states of operation of the unit microfluidic device of FIG. 8 in accordance with various aspects of the subject disclosure.

FIGS. 12A-12D illustrate additional experimental data demonstrating the effectiveness of target cell electroporation and transfection in accordance with various aspects of the subject disclosure.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Systems and methods are disclosed herein that can be employed in a transfection process involved in CAR-T (chimeric antigen receptor T-cell) and other cell modification. Other example uses of the technology disclosed include protein and virus production, reprogramming of stem cells, silencing of particular genes for treatment of genetic diseases, or siRNA delivery. Other uses of the systems and methods disclosed herein can be implemented without departing from the scope of this disclosure.

More generally, the systems and methods disclosed herein can be used to enhance the process of cargo delivery to cells, vesicles, micelles, and exosomes (herein referred to as targets) via electroporation. Cargo can include, but is not limited to, DNA, RNA, proteins, transposons, and biomolecule complexes. The systems and methods disclosed herein can help improve transfection efficiency, maintain viability/integrity of targets going through the process, and regulate the amount of cargo that enters the targets. The systems and methods disclosed herein include microfluidic devices that provide for precision manipulation of the spatial position of the targets, while maintaining rapid, efficient and scalable cell processing capabilities.

In accordance with various aspects of the disclosure, the targets are flowed toward a semipermeable membrane in a microfluidic device and temporarily immobilized, thereby facilitating precise positioning and thus controlled exposure of the targets to an electric field for electroporation.

Figure 1:
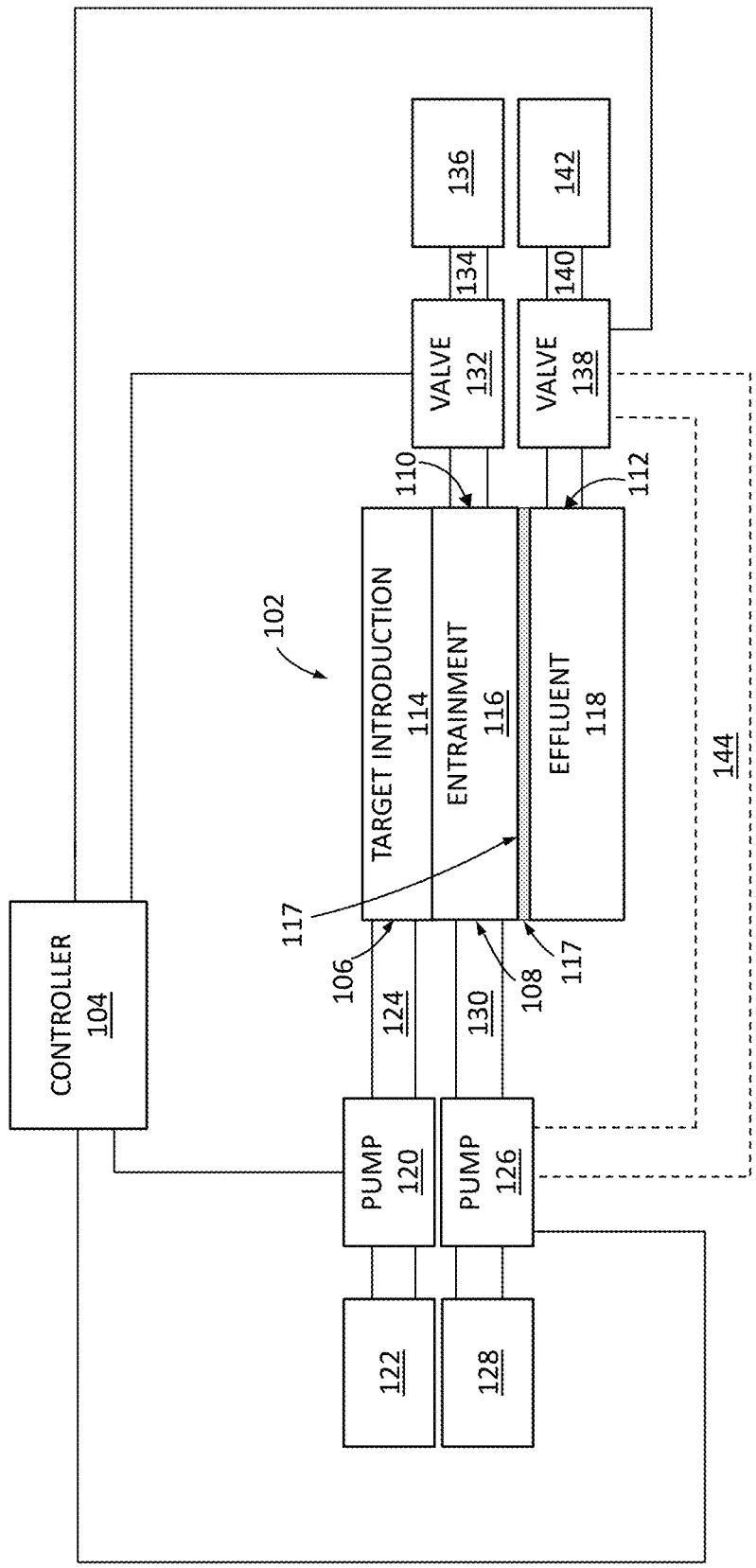
FIG. 1 is a block diagram of an example system including a microfluidic device in accordance with various aspects of the subject disclosure.

FIG. 1 shows a block diagram of a system 100 such as a biological material delivery system. As shown, system 100 includes a microfluidic delivery device 102 (sometimes referred to herein as a microfluidic device or device), a target reservoir 122, an effluent reservoir or source 128, pumps such as pumps 120 and 126 for respectively flowing targets and cargo from target reservoir 122 and effluent reservoir 128 into the microfluidic device, valves such as valves 132 and 138 for controlling the path of fluid flow out of the delivery device, and a controller 104 (e.g., a computer processor) for controlling the pumps 120 and 126, the valves, 132 and 138, and the application of electrical signals to electroporation electrodes included in the microfluidic device (as described in further detail hereinafter).

As shown in FIG. 1, the microfluidic device 102 is a multi-layer structure, including a target introduction layer or substrate 114, a target entrainment layer or substrate 116, and an effluent layer or substrate 118, each stacked onto another vertically. As shown, a membrane 117 is positioned between the target entrainment layer 116 and the effluent layer 117. In some implementations, target introduction layer 114 and target entrainment layer 116 are formed (e.g., etched, milled, or otherwise patterned or micromachined) in a common substrate (e.g., to form a single layer with target introduction and entrainment channels).

Membrane 117 is a semipermeable membrane that is impermeable to the target, but permeable to fluid and can be either permeable or impermeable to cargo. Membrane 117 can be, for example, a track-etched membrane with a thickness of between 10-20 µm. For example, a surface of membrane 117 in a target entrainment channel in entrainment substrate 116 may include pores that can vary in size depending on the particular target and particular cargo intended to be used in the device. As such, the pores can range from between 5 nm and 20 µm in diameter. In some implementations, such as for use with T-cells, the pores can be about 3 µm in diameter.

As shown in FIG. 1, pumps 120 and 126 may be coupled to microfluidic device 102 by respective fluid lines 124 and 130 that are respectively fluidly coupled to target introduction port 106 and effluent introduction port 108. Valves 132 and 138 are operable by controller 104 to control the flow of fluid within microfluidic device 102 and from microfluidic device 102 to target collection reservoir 136 and/or effluent collection reservoir 142 respectively through target outlet port 110 and/or effluent outlet port 112 (e.g., through respective fluid lines 124 and 140) as described in further detail hereinafter.

In some implementations, reservoirs 122, 128, 136, and 142 may each be implemented as any type of fluid containing vessel. In some implementations, one or more of reservoirs 122, 128, 136, and 142 may be implemented as a transwell or well plate housing a mixture of fluid and cells. In some implementations, pumps 120 and/or 126 may be implemented as peristaltic pumps or syringe pumps. In some implementations, each of the pumps 120 and 126 is a different type of pump. For example, the microfluidic channels in microfluidic device 102 can be coupled to a peristaltic pump and other fluid flow lines or channels such as manifold channels can be coupled to a syringe pump. Pumps 120 and/or 126 are operable by controller 104 to control the fluid flowing through microfluidic device 102. For example, pumps 120 and/or 126 can control the fluid's flow rate, flow profile (e.g., whether the flow is pulsatile or smooth), and shear rate. In some implementations, the flow is continuous and in other implementations the flow is pulsatile. The fluids that pass through the microfluidic device 102 can include, but are not limited to, cell culture medium, cell nutrients, reagents, test agents, buffer fluids, tracer particles, gases, reactant fluids, fixing agents, stains, simulated and real biological fluids such as blood filtrate, whole blood, blood serum, blood plasma, urine, dilute urine.

In the example of FIG. 1, system 100 includes an effluent collection reservoir 142. Effluent reservoir 142 collects fluid exiting microfluidic device 102. However, in some implementations, system 100 may be provided without an effluent reservoir, and as a closed-loop system having a flowback fluid line 144 through which fluid exiting outlet port 112 microfluidic device 102 can be routed back into inlet port 108 of microfluidic device 102.

In the example of FIG. 1, target reservoir 122 may store targets and cargo together for flow into microfluidic device together. However, it should be appreciated that system 100 may be provided with a separate cargo reservoir for flow of cargo into microfluidic device 102 before or after the targets have been provided into the microfluidic device.

It should also be appreciated that microfluidic device 102 may include multiple unit microfluidic devices, each having structures (e.g., microfluidic channels formed from layers 114, 116, 117, and 118 and electrodes) for electroporation of targets and each coupled, via a manifold that is not explicitly shown in FIG. 1 but that is described in further detail hereinafter (see, e.g., FIG. 5), to fluid lines 124, 130, 134, and 140. In other implementations, microfluidic device 102 may be a standalone device that is directly fluidly coupled to fluid lines 124, 130, 134, and 140 as shown in the schematic example of FIG. 1.

Figure 2:
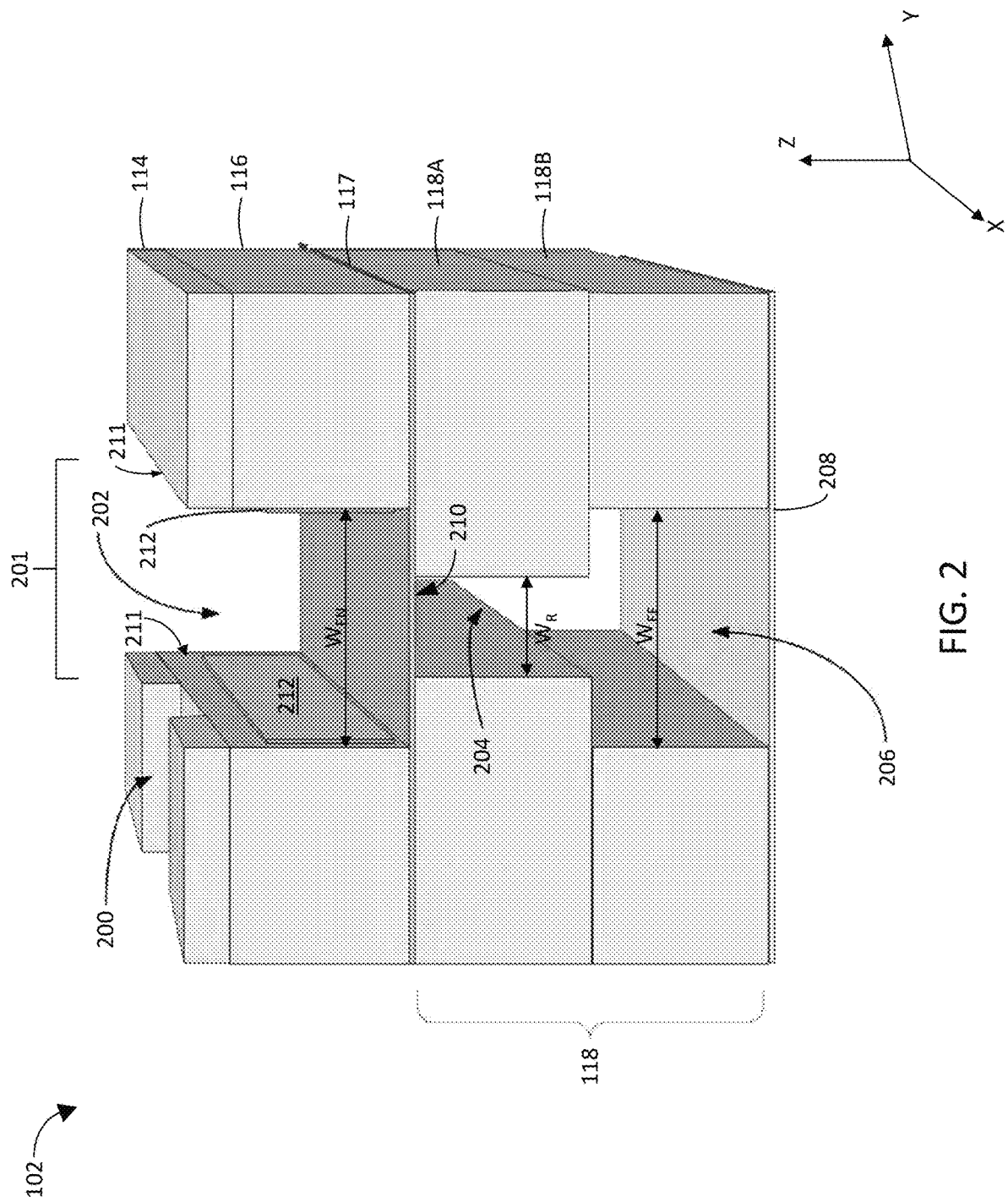
FIG. 2 shows a cutaway perspective view of a portion of a microfluidic device in accordance with various aspects of the subject disclosure.

FIG. 2 shows a cutaway perspective view of a portion of microfluidic device 102, showing target introduction layer 114 with a target introduction channel 200, target entrainment layer 116 having a target entrainment channel 202, and effluent layer 118 having an effluent channel 206. A bottom coversheet 208 is also shown sealing the bottom of effluent layer 118 and effluent channel 206. A top coversheet over target introduction channel 200 may also be provided, but is omitted in FIG. 2 to avoid obscuring the view into the device. Also viewable in FIG. 2 are electrodes 212 positioned on the sidewalls 211 of target entrainment channel 202.

As shown in FIG. 2, target introduction layer 114 may be formed from a first substrate having a first channel 200 that forms the target introduction channel and another channel that corresponds in size, location, and shape to target entrainment channel 202. It should also be appreciated that target introduction channel 200 may be formed in a common substrate with target entrainment channel 202 in some implementations. In the example shown in FIG. 2, target entrainment layer 116 is formed from a second substrate having a first side attached to the first substrate (114), an opposing second side, and includes a second channel that extends from the first side to the opposing second side to form the target entrainment channel. However, it should be appreciated that in other implementations, the second channel (target entrainment channel) can be a trench that extends only partially between the first and second sides (e.g., from the opposing second side partway to the first side so that a portion of the substrate forms a lid or cover for channel 202). Electrodes 212 are operable by controller 104 to generate an electric field in the target entrainment channel.

As shown in FIG. 2, semipermeable membrane 117 has a first side that is attached to the opposing second side of the second substrate (116) and spans the target entrainment channel to form a floor of that channel. Effluent layer 118 is formed from a third substrate 118A/118B that is attached to an opposing second side of semipermeable membrane 117 and that has a third channel that is adjacent the semipermeable membrane to form a restrictor channel 204 and a fourth channel that is fluidly coupled to the restrictor channel 204 to form an effluent channel 206. Layers 114, 116, and/or 118 may be attached to each other using a clamp or other external attachment mechanism or may be attached to each other using attachment mechanisms at the interface between two layers such as an adhesive, ultrasonic weld, or the like.

As shown in FIG. 2, target entrainment channel 202, restrictor channel 204, and effluent channel 206 are coaligned to form a main channel 201 in microfluidic device 102 and each have an elongate dimension that is parallel to the semipermeable membrane (e.g., along the x-direction of FIG. 2). Target introduction channel 200 has an elongate dimension that is not parallel (e.g., perpendicular along the y-direction of FIG. 2) to the elongate dimension of main channel 201. As shown, effluent channel 206 has a width $W_{EF}$ that is relatively wider than the width $W_R$ of restrictor channel 204 in a direction (e.g., the y-direction) that is parallel to the semipermeable membrane and perpendicular to the elongate dimensions of target entrainment channel 202, restrictor channel 204, and effluent channel 206. As discussed in further detail hereinafter, providing a restrictor channel 204 interposed between membrane 117 and effluent channel 206 generates a fluid flow in target entrainment channel 202 that urges target cells away from sidewalls 211 toward a center of target entrainment channel 202.

In this way, a microfluidic device is provided in which target entrainment layer 116 includes a channel that is above membrane 117. In the example of FIG. 2, target entrainment channel 206 has a rectangular cross-section and a width $W_{EN}$ (e.g., in the y-direction of FIG. 2). Effluent layer 118, which is below the membrane 117, includes an effluent channel 206 which, in combination with restrictor channel 204, forms a channel within effluent layer 118 that has an upside-down, T-shaped cross-section. The narrow part of the upside-down, T-shaped cross-section channel (referred to as the restrictor channel 204 and having a width $W_R$) is adjacent to a bottom side of membrane 117, and the wide part of the upside-down, T-shaped cross-section channel forms effluent channel 206, where restrictor channel 204 is interposed between membrane 117 and effluent channel 206.

Effluent channel 206 has a width $W_{EF}$ along the y-direction of FIG. 1, which can be the same as width $W_{EN}$ of target entrainment channel 202 (though in some implementations, the width $W_{EF}$ of the effluent channel may be wider or narrower than the width $W_{EN}$ of target entrainment channel 202 so long as width $W_{EF}$ is wider than width $W_R$ of restrictor channel 204 so that flow of fluid through membrane 117 and restrictor 204 into effluent channel 206 urges target cells away from sidewalls 211 toward the center of entrainment channel 202. As shown in FIG. 2, effluent layer 118 may itself be formed from the stacking of two substrates 118A and 118B having different width channels 204 and 206 formed respectively therein. However, in some implementations, the effluent channel 206 and restrictor channel 204 are formed in a single substrate. Top and bottom cover sheets (see, e.g., bottom cover sheet 208) may seal the top and bottom of the microfluidic device respectively.

Each of layers 114, 116, and 118 can be made of substrates formed from polystyrene, polycarbonate, polyimide, polyetherimide (PEI), polysulfone, polyethersulfone, acrylic, or cyclic olefin copolymer (COC), biodegradable polyesters, such as polycaprolactone (PCL), soft elastomers such as polyglycerol sebacate (PGS), other thermoplastics or other structural materials. The substrates may alternatively be made of polydimethylsiloxane (PDMS), poly(N-isopropylacrylamide), polyurethane (PU), fluorinated ethylene propylene (FEP), or a fluoropolymer elastomer. In some implementations, one or more of the substrates can be formed from glass, a ceramic, or a semiconductor, such as Silicon (Si). The flow channels described herein can be generally rectangular or square shaped or can have a circular, oval, hexagonal, or other geometric or irregular shape.

In some implementations, membrane 117 may be made of a thermoplastic, such as polystyrene, polycarbonate, polyimide, polysulfone, polyethersulfone; biodegradable polyesters, such as polycaprolactone (PCL); soft elastomers, such as polyglycerol sebacate (PGS); or other polymers such as polydimethylsiloxane (PDMS) and poly(N-isopropylacrylamide). In other implementations, membrane 117 is made from silicon, glass, or silicon nitride. In yet other implementations, membrane 117 is a multilayered membrane that includes several layers of material.

Figure 3A:
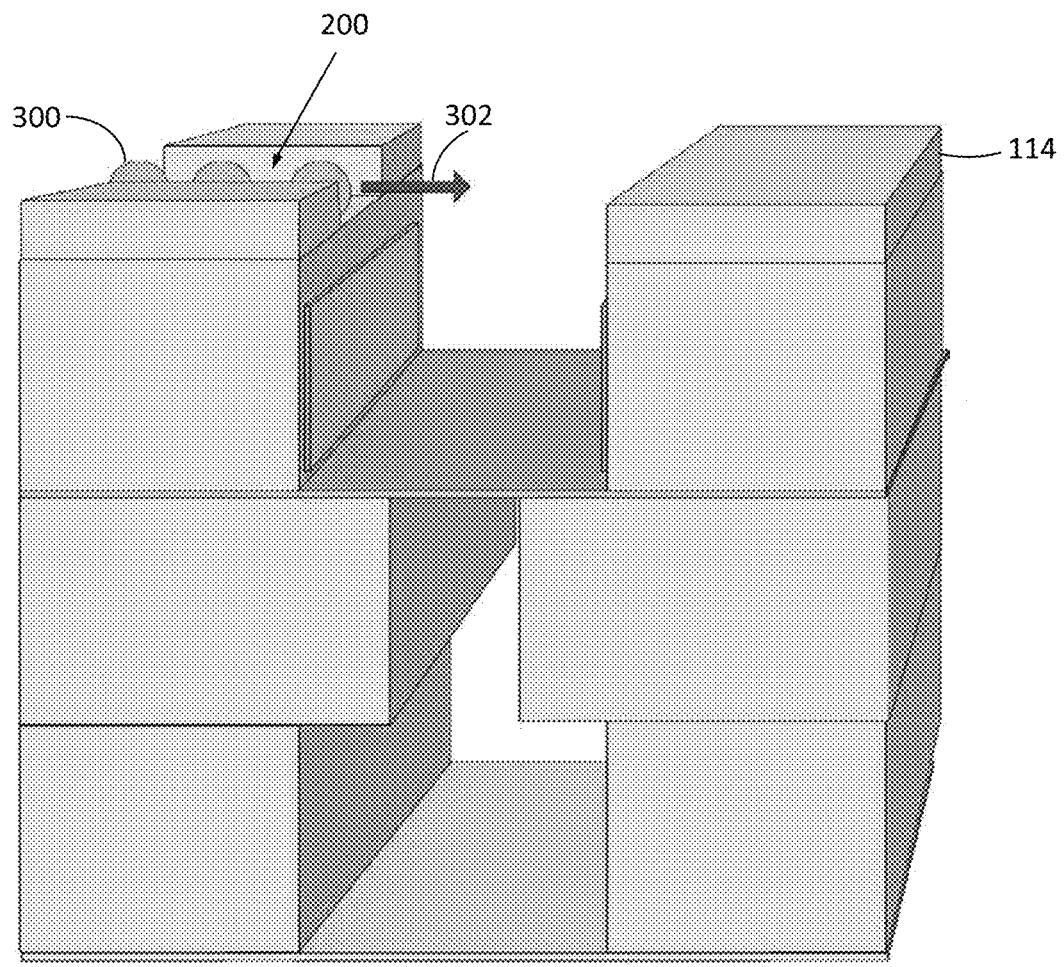
Figure 3B:
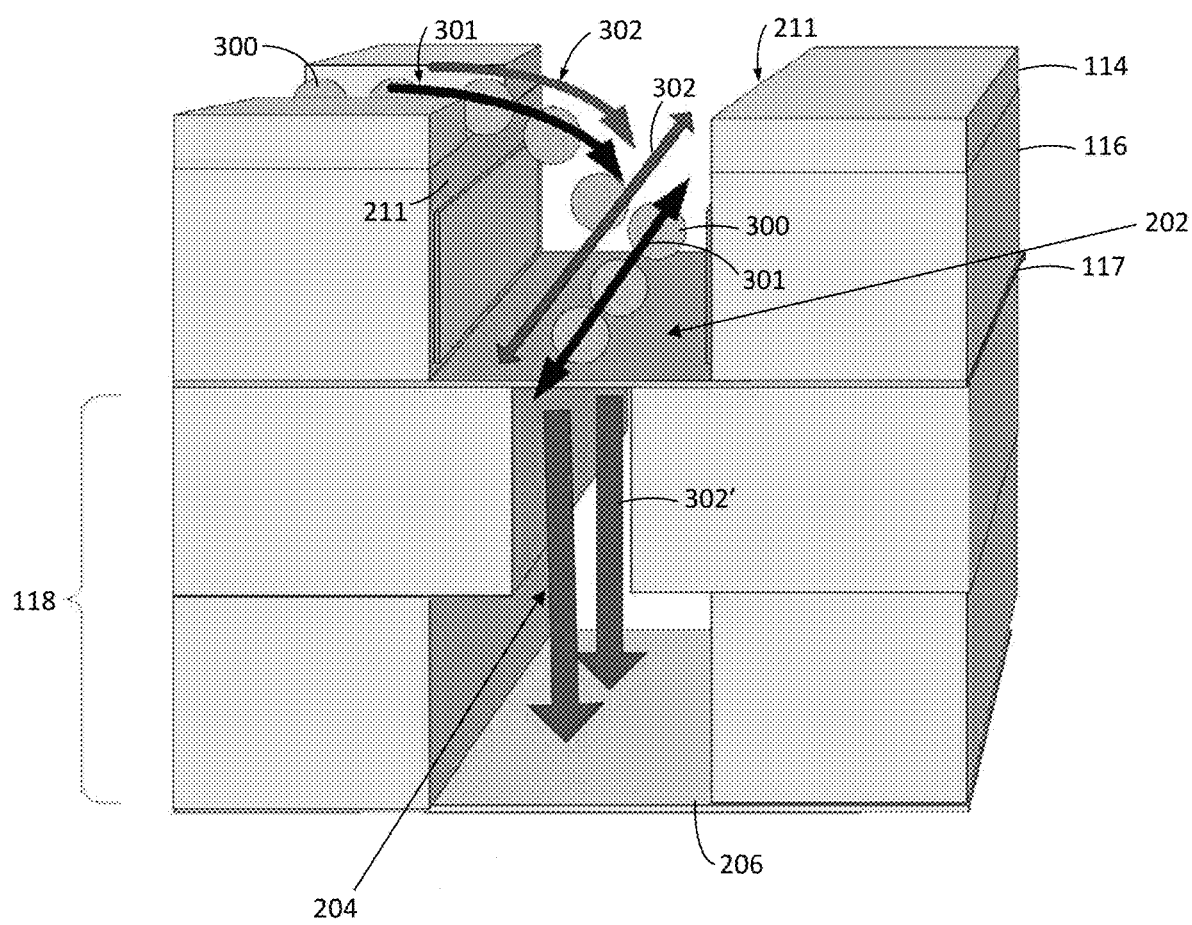

FIGS. 3A-3E show the cutaway perspective view of FIG. 2 at various stages during the operation of system 100 in accordance with aspects of the disclosure. As shown in FIGS. 3A and 3B, targets 300 are introduced into target entrainment channel 202 (target path shown with arrows 301) from target introduction channel 200 formed in target introduction layer 114. In this example, targets 300 are suspended in a fluid that flows (fluid flow path shown with arrows 302) through target introduction channel 200, into and along target entrainment channel 202 and, in part, through membrane 117 into effluent channel 206 via restrictor channel 204 (as indicated by fluid flow arrows 302' on the bottom side of membrane 117). The fluid may then flow along and out effluent channel 206 via outlet port 112 (FIG. 1).

FIG. 3C illustrates how the presence of restrictor channel 204, and the width of restrictor channel 204 relative to effluent channel 206 and/or entrainment channel 202, causes targets 300 to line up on the membrane substantially in the center of the target entrainment channel 202 (see, e.g., FIGS. 4 and 10 for further details), after targets 300 are introduced into target entrainment channel 202 and distributed and/or pinned (e.g., immobilized or held in position) onto top surface 320 of membrane 117 by flow of fluid through membrane 117 and restrictor channel 204.

Figure 3D:
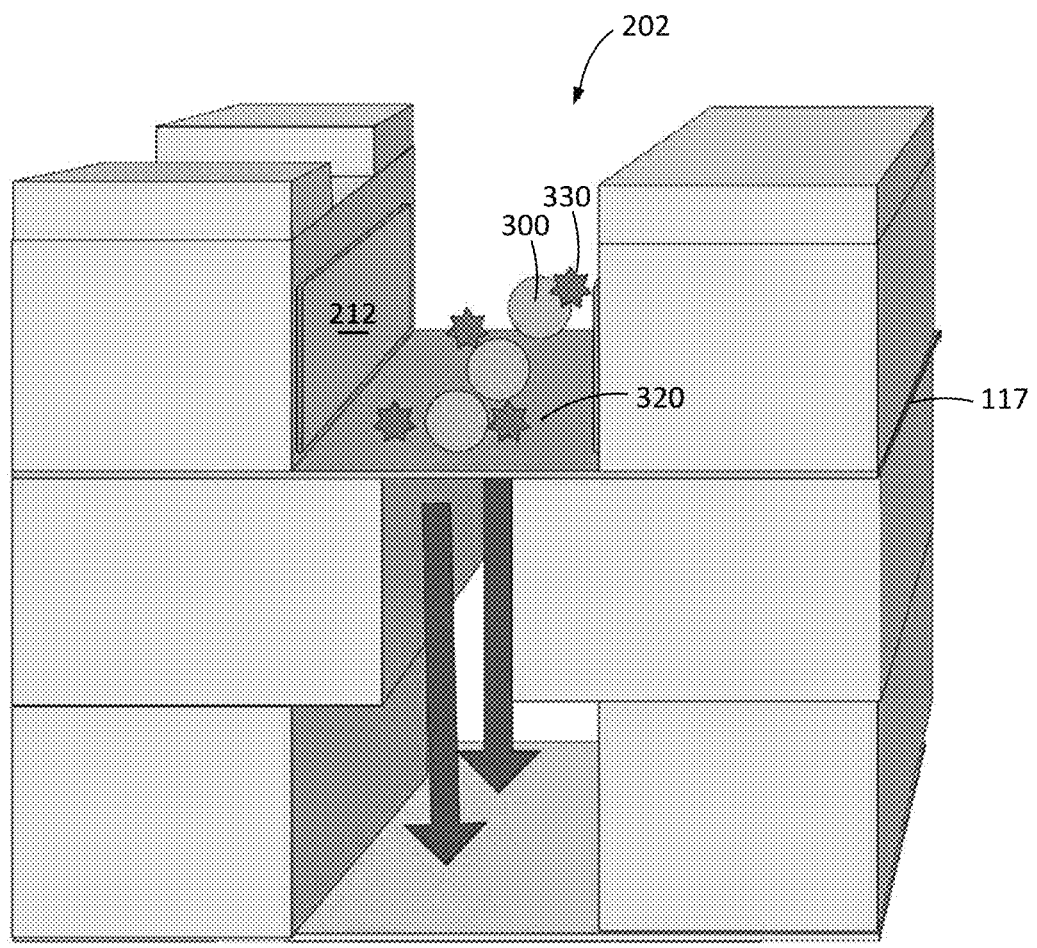

Electrodes 212 may be patterned onto sidewalls 211 of target entrainment channel 202 and can be energized by voltage drivers controlled by controller 104 to deliver electroporation pulses or waveforms to targets 300 in channel 202. The voltage drivers can integrated into the controller 104 or can be standalone components controlled by the controller 104. Cargo 330 to be delivered into targets 300 are shown in FIG. 3D. Cargo elements 330 can be introduced along with targets 300, after targets 300 are pinned on membrane 117 in the target entrainment channel, or can be preloaded onto membrane 117 prior to the introduction of targets 300 into channel 202.

Because targets 300 are held in position in target entrainment channel 202 by active flow of fluid through membrane 117 and restrictor channel 204 and out of the device via effluent channel 206, heat that is generated by electrodes 212 is convectively removed from channel 202 during electroporation. In this way, the temperature of targets 300 and cargo 330 can be regulated to enhance the viability of transfected cells.

Figure 3E:
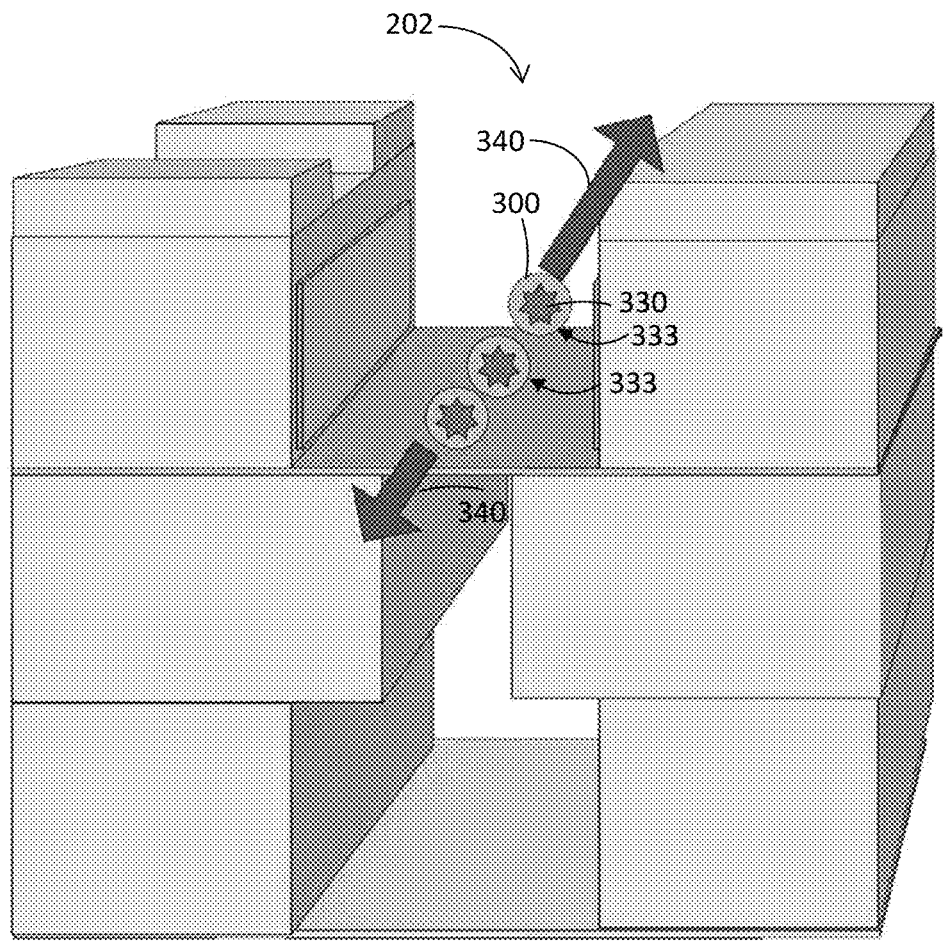

FIG. 3E illustrates how, after electroporation of targets 300 using electric fields generated in channel 202 by electrodes 212, at least some of cargo elements 330 have entered respective targets 300, and the cargo-carrying targets 333 are removed by flowing along entrainment channel 202, as indicated by arrows 340, through outlet port 110 (FIG. 1).

In one implementation, the microfluidic geometry of microfluidic device 102 is designed for T-cells as targets 300. In such an implementation, target entrainment channel 202 can have a length along the x-direction of FIG. 2 of about 5 millimeters (mm), a height along the z-direction of FIG. 2 of about 120-300 microns (µm) (e.g., 254 µm), and a width $W_{EN}$ along the y-direction of FIG. 2 of about 80-200 µm (e.g. 150 µm). Restrictor channel 204 can be about 5 mm long (x-direction), 125-135 µm (e.g., 127 µm) tall (in the z-direction), and about 40-60 µm (e.g. 50 µm) wide (in the y-direction). Effluent channel 206 can have similar dimensions to those of target entrainment channel 202, though in some implementations, effluent channel 206 may be taller, e.g., between about 450-550 µm (e.g., 510 µm) than target entrainment channel 202. The channels are depicted in FIGS. 2-3E as being rectilinear channels with planar sidewalls and hard corners, however, it should be appreciated that the sidewalls and/or corners of one or more of the depicted channels can be rounded or otherwise shaped.

Figure 4:
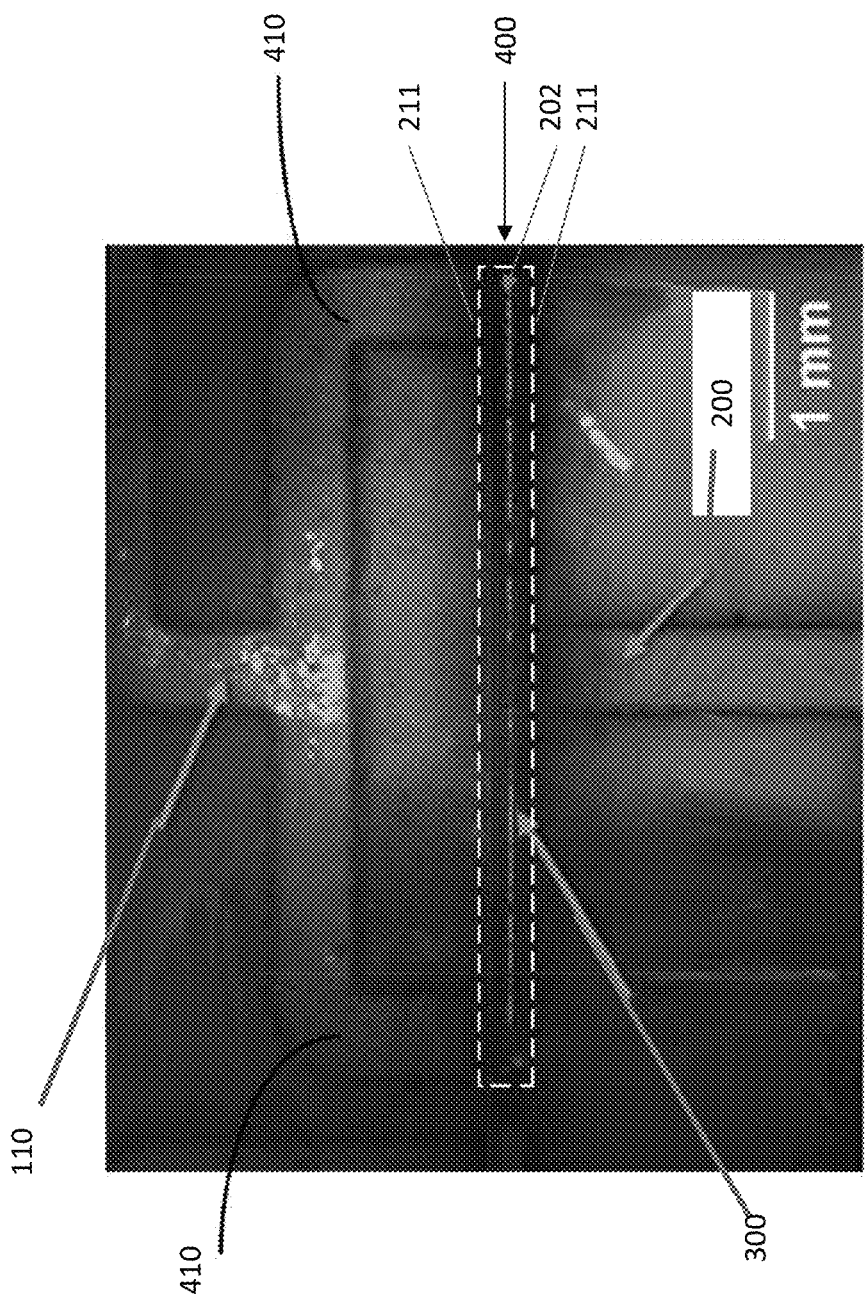
FIG. 4 illustrates a top view of a portion of a microfluidic device in accordance with various aspects of the subject disclosure.

FIG. 4 illustrates a top-down microscope view of a portion of microfluidic device 102 demonstrating the efficacy of the fluid flow described above in connection with FIGS. 3A-3E (e.g., through membrane 117 and restrictor channel 204 into effluent chamber 206), in entraining targets 300 such as 10-micron latex beads or T-cells along a clear, well-defined line along the center 400 of target entrainment channel 202. FIG. 4 also shows an exemplary arrangement of target outlet channels 410 through which targets 300 flow out of target entrainment channel 202 to outlet port 110 after electroporation and cargo delivery (as previously described and illustrated in connection with FIG. 3E). In the implementation illustrated in FIG. 4, target outlet channels 410 are formed in target entrainment layer or substrate 116. Target introduction channel 200 can also be seen in the top view of FIG. 4. In this example, to flow transfected cells out of target entrainment channel 202, additional fluid may flow, for example, from target introduction channel 200, into and within target entrainment channel 202, and through target outlet channels 410 to outlet port 110.

Figure 6:
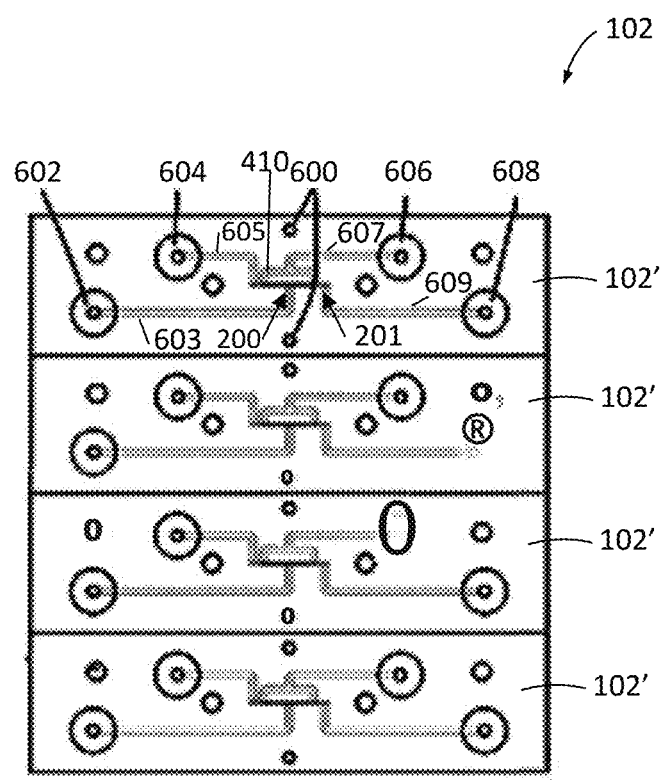
FIG. 6 illustrates a top view of a microfluidic device that includes multiple, linearly separated unit microfluidic devices in a common package in accordance with various aspects of the subject disclosure.
Figure 7:
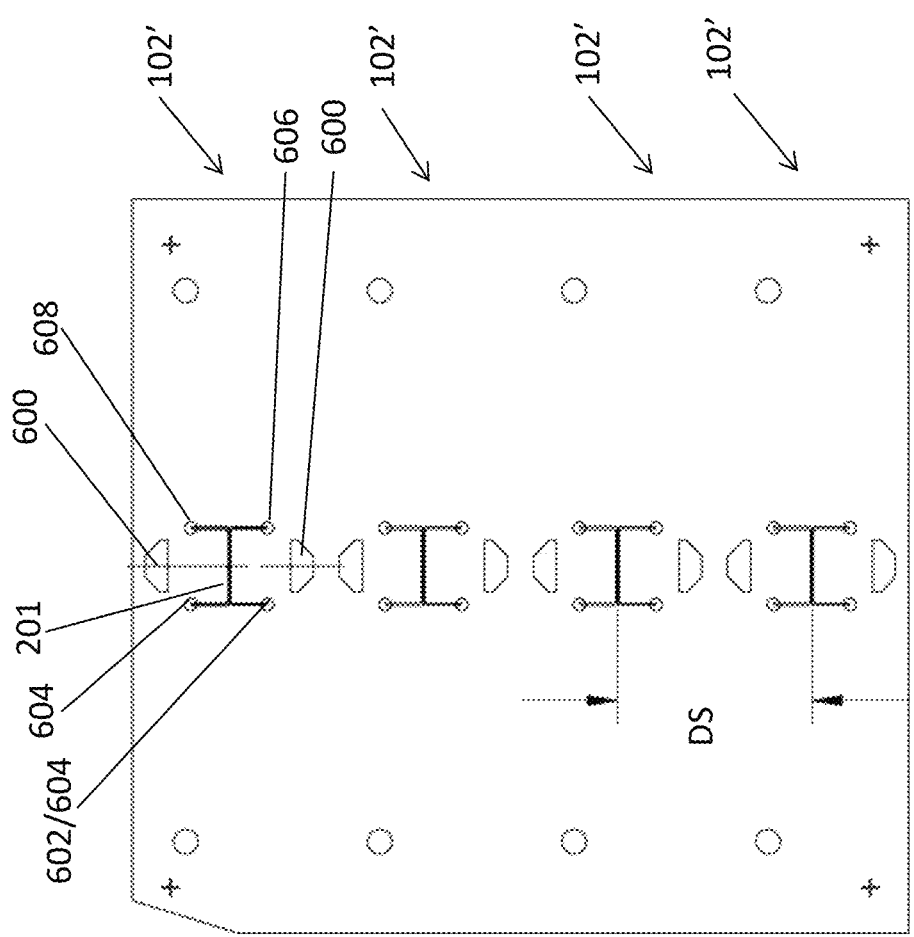
FIG. 7 illustrates another top view of a microfluidic device that includes multiple, linearly separated unit microfluidic devices in a common package in accordance with various aspects of the subject disclosure.

The geometry of the portions of device 102 described above in connection with FIGS. 2-4 can represent a single parametric unit microfluidic device that can be patterned in an array (along with appropriate manifolding) for scaling up to processes large numbers (e.g., billions) of targets. In the example of T-cell processing discussed above, a single set of stacked channels may process approximately 500-1000 cells at once. Examples of layouts for an array of multiple unit microfluidic devices are shown in FIGS. 5, 6, and 7.

Figure 5:
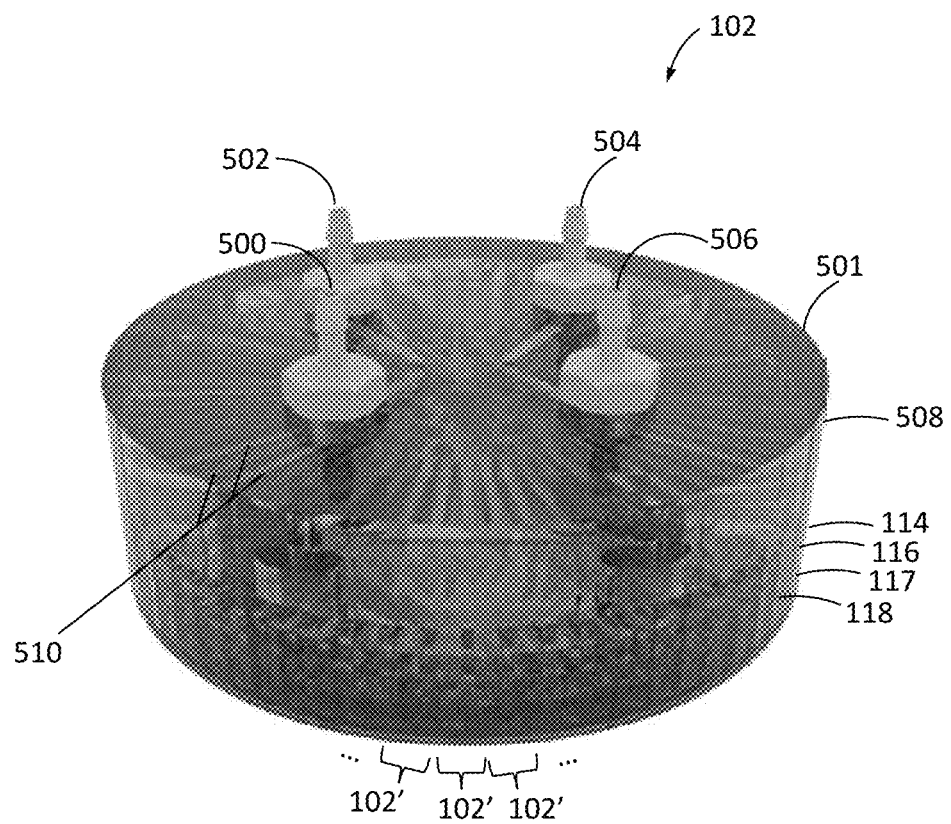
FIG. 5 illustrates a perspective view of a microfluidic device that includes multiple, angularly separated unit microfluidic devices in a common package in accordance with various aspects of the subject disclosure.

As shown in FIG. 5, microfluidic device 102 may be implemented with multiple unit microfluidic devices 102' (each as shown and described above in connection with FIGS. 2-4) angularly separated within a common package 501. In this example, a manifold layer 508 is formed over target introduction layer 114, and target introduction layer 114, target entrainment layer 116, and effluent layer 118 of each unit microfluidic device 102' are formed as portions of a common substrate in which the channels described above are formed. Membrane 117 may form a continuous layer in device 102 of FIG. 5 or can be formed from separate membrane portions 117 for each unit device 102'.

Manifold layer 508 includes a network of manifold channels 510 that fluidly couple a target inlet port, an effluent inlet port, a target outlet port, and an effluent outlet port of each unit microfluidic device 102' to a common target inlet port 500, a common effluent inlet port 502, a common target outlet port 504, and a common effluent outlet port 506 for the overall device 102. Common target inlet port 500, common effluent inlet port 502, common target outlet port 504, and common effluent outlet port 506 may correspond, respectively, to ports 106, 108, 110, and 112 of FIG. 1.

However, it should be appreciated that the circular arrangement of unit devices 102' of FIG. 5 is merely illustrative and other arrangements are contemplated. For example, FIG. 6 shows and example top view of microfluidic device 102 in which unit microfluidic devices 102' are linearly separated from each other. In the example of FIG. 6, each effluent channel has a separate inlet 604 for accepting flow in addition to flow received through the membrane.

In this example, a manifold layer that fluidly couples common target inlet port 500, common effluent inlet port 502, common target outlet port 504, and common effluent outlet port 506 to respective unit device target inlet port 602, unit device effluent inlet port 604, unit device target outlet port 606, and unit device effluent outlet port 608 is omitted from the figure for clarity, and so that electrical contacts 600 of each unit device can be seen. Electrical contacts 600 couple controller 104 to electrodes 212 in each unit microfluidic device 102'. In the example of FIG. 6, unit device target inlet port 602, unit device effluent inlet port 604, unit device target outlet port 606, and unit device effluent outlet port 608 are fluidly coupled to main channel 201 of each unit microfluidic device 102' by a respective fluid path 603, 605, 607, and 609 that each include at least a portion that extends in a direction parallel to main channel 201 (e.g., in layer 114 or 116).

In the example of FIG. 6, fluid may flow from target inlet port 602, through target introduction channel 200 to main channel 201 as described above in connection with FIGS. 2-4. Cargo-carrying targets may be removed from main channel 201 as described above in connection with FIG. 4 (e.g., using additional fluid, from inlet port 602 through main channel 201 and target outlet channels 410, to fluid path 607 to target outlet 606) and/or using additional fluid introduced from effluent inlet port 604. While fluid flows through the membrane in main channel 201 to hold target cells therein, fluid may flow out from effluent channel 206 to fluid path 609 and effluent outlet port 608 (for example). Unit device ports 602, 604, 606, and 608 may be formed on a top surface of each unit device as shown in the example of FIG. 6, or one or more of unit device ports 602, 604, 606, and 608 may be formed along the side or edge of a corresponding layer or substrate of device 102.

Figure 8:
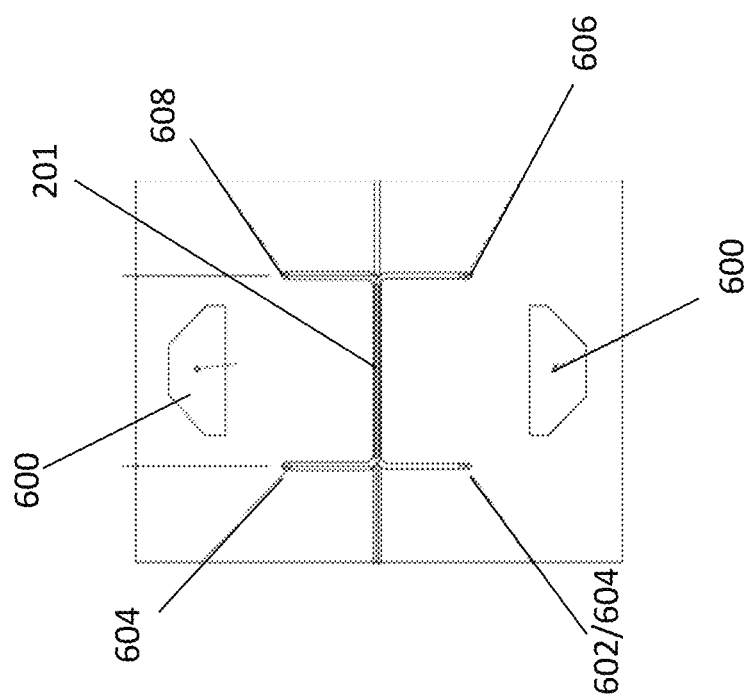
FIG. 8 illustrates a unit microfluidic device of the microfluidic device of FIG. 7 in accordance with various aspects of the subject disclosure.

FIG. 7 illustrates a top view of another linear arrangement of unit microfluidic device 102' in a common package. In the example of FIG. 7, unit microfluidic devices 102' are linearly separated from each other by a distance DS of between 12 and 13 mm (for example). In the example of FIG. 7, unit device target inlet port 602, unit device effluent inlet port 604, unit device target outlet port 606, and unit device effluent outlet port 608 are fluidly coupled to main channel 201 of each unit microfluidic device 102' by a respective fluid path 603, 605, 607, and 609 that each extend in a direction perpendicular to main channel 201. An enlarged top view of one of the unit microfluidic devices 102' of FIG. 7 is shown in FIG. 8 for clarity. It should be appreciated that the arrangements of FIGS. 6 and 7 differ in the geometric arrangements of some parts, but that both arrangements include substantially the cross-sections and functional parts within main channel 201. The arrangement shown in FIGS. 7 and 8 may be beneficial to improve bonding between the layers and prevent leaking.

FIGS. 9A, 9B, and 9C illustrate top views of main channel 201 at various stages of an electroporation process corresponding respectively, for example, to the stages described above in connection with FIGS. 3A, 3D, and 3E, but using the microfluidic device as implemented in FIGS. 7 and 9.

In the example of FIGS. 7-9, a first u-shaped channel between target/effluent inlet port 602/604 and target outlet port 606 is formed in target entrainment layer 116 and includes a portion corresponding to target entrainment channel 202. In the example of FIGS. 9A, 9B, and 9C, a portion of membrane 117 that is exposed in the target entrainment channel 202 of main channel 201 is visible. In the example of FIGS. 7-9, a second u-shaped channel between effluent inlet port 604 and effluent outlet port 608 is formed in effluent layer 118 and includes a portion corresponding to effluent channel 206 (formed below the visible portion of membrane 117 and below an interposing restrictor channel as in FIGS. 2-3E).

In the example of FIG. 9A, target cells 300 and cargo 303 are loaded from a common reservoir 122 into the device via inlet port 602. In the example of FIG. 9B, target outlet port 606 is blocked so that target cells 300 are pinned and temporarily immobilized by flow of fluid from inlet 602/604, and onto and through porous membrane 117 integrated into the main channel 201 (e.g., forming a floor of entrainment channel 202). As shown, fluid that has passed down through membrane 117 and restrictor channel 204 is allowed to flow out of port 608 at this stage. Once target cells 300 are pinned on membrane 117, one or more voltage pulses are applied to electrodes 212 to generate an electric field 900 in the channel.

As shown in FIG. 9C, after electroporation by electric field 900 and resulting absorption of cargo elements 330, cargo-carrying target cells 333 (e.g., transfected cells) are unpinned and removed from the device by opening target outlet port 606 to allow flow to reservoir 136 (FIG. 1).

To flow cargo-carrying target cells 333 from target entrainment channel 202 through target outlet port 606, additional fluid can be flowed into effluent inlet port 604 and effluent outlet port 608, to pass up through restrictor channel 204 and membrane 117 (e.g., in a direction opposite to the direction of flow for pinning targets against membrane 117) and out through target outlet port 606, as illustrated in FIG. 9C. In this example, a valve may be closed by controller 104 to prevent backflow through port 602/604 into reservoir 122.

Figure 10A:
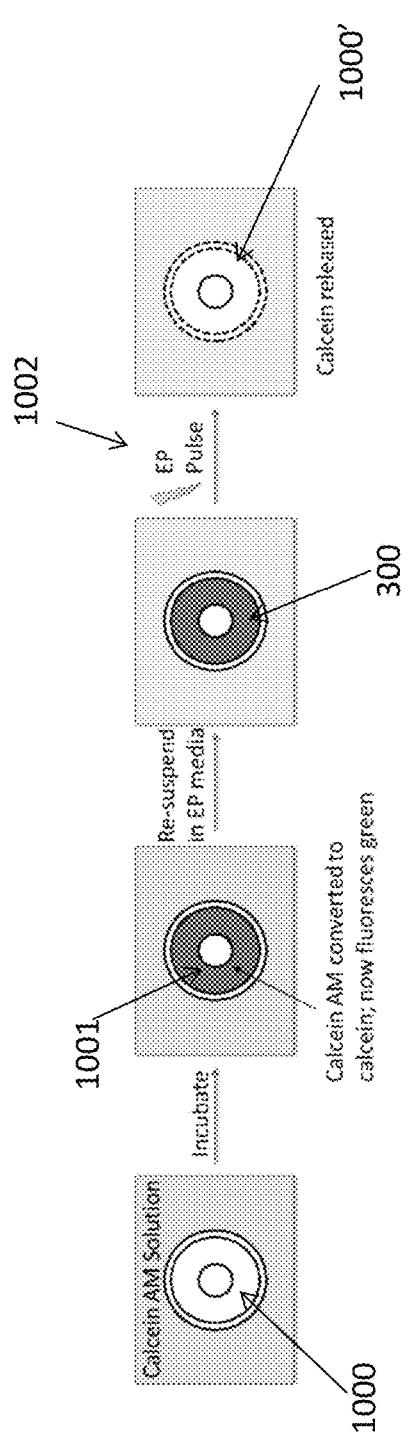
FIGS. 10A-10E illustrate experimental data demonstrating the effectiveness of target cell positioning and electroporation in accordance with various aspects of the subject disclosure.

FIGS. 10A-10E illustrate experimental data demonstrating the effectiveness of cell permeabilization in microfluidic device 102. As illustrated in FIG. 10A, primary human T cells 1000 are labeled with calcein 1001 by first incubating with Calcein AM solution. Calcein AM only becomes fluorescent after being taken up by live cells and converted into calcein by intracellular esterases. Once converted into calcein 1001, the molecule cannot penetrate through the cell membrane.

Figure 10B:
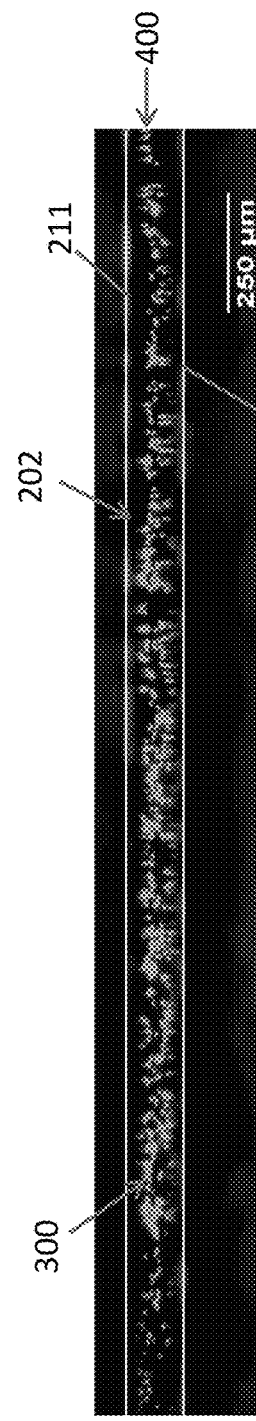

As shown in FIG. 10B, calcein-labelled primary human T cells, now representing target cells 300 in FIGS. 10A and 10B, were loaded into microfluidic device 102 and then fluidically pinned onto membrane 117. FIG. 10B shows how the restrictor channel geometry as described herein helps to keep cells 300 away from the sidewalls 211 and the electrodes 212 formed thereon (e.g., by the flow of fluid through membrane 117 and restrictor channel 204 to effluent channel 206).

Figure 10C:
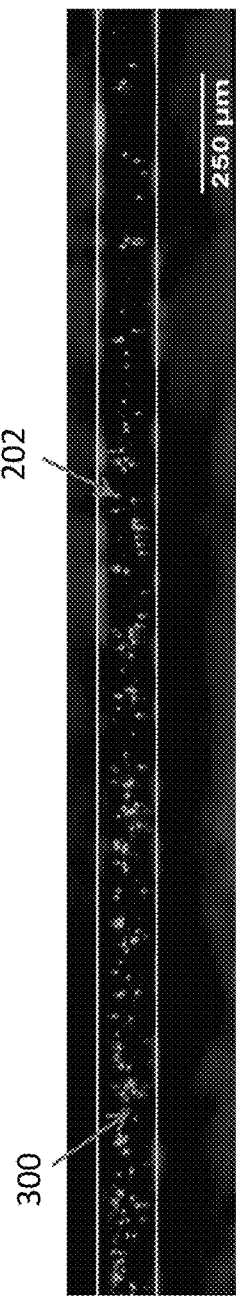
Figures 10D, 10E:
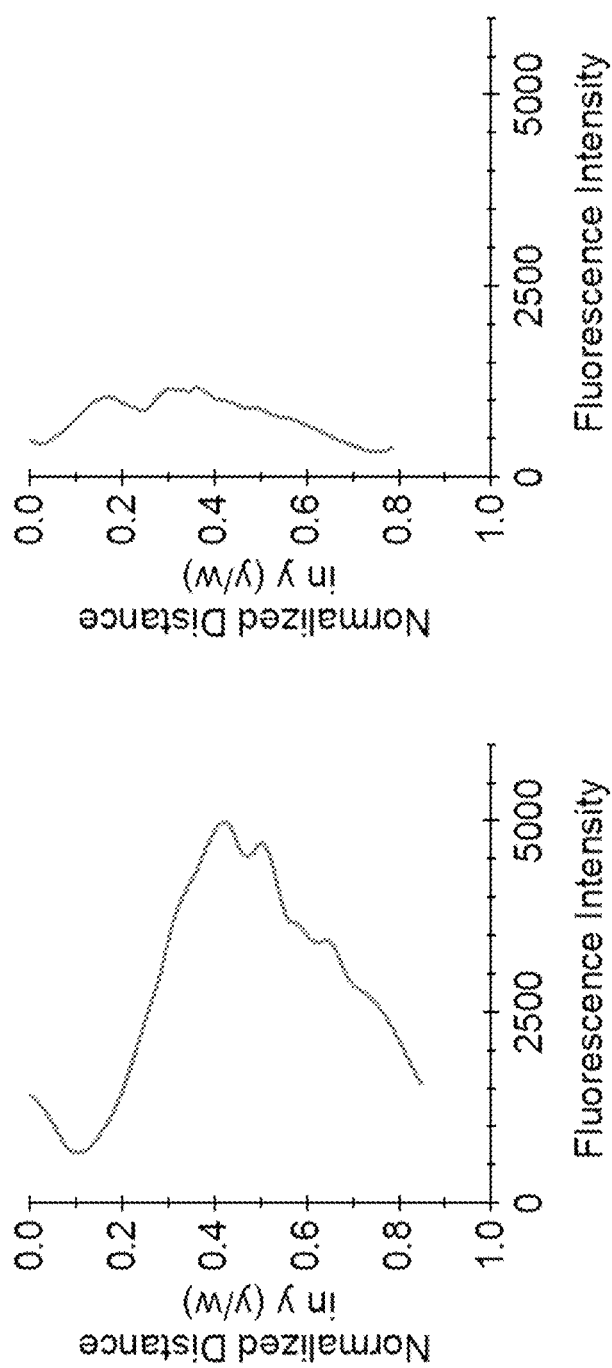

Returning to FIG. 10A, following one or more electrical (electroporation or EP) pulses 1002, target cells 300 are electroporated and the calcein is released from within the cells. FIG. 10C shows how the electroporated cells 1000' having released the calcein are no longer visible in channel 202. As shown in FIG. 10D, the average fluorescence signal across the channel width in FIG. 10B shows that the cells 300 were preferentially distributed to the center of the channel 202, away from the sidewalls 211. FIG. 10C shows that, after electroporation, over 70% of the cells 300 were peremabilized and lost calcein signal, attendant with a decrease in average fluorescence across the channel as shown in FIG. 10E. In this experimental example, the number of cells that lost calcein signal increased as expected with the amount of energy delivered by electroporation pulses. After five pulses had been delivered, over 70% of the cells had lost calcein signal. Pulse voltages ranged from 10 to 25 V, and pulse durations ranged from 100 µs to 200 µs. The distance between the electrodes was 150 µm.

Figure 11:
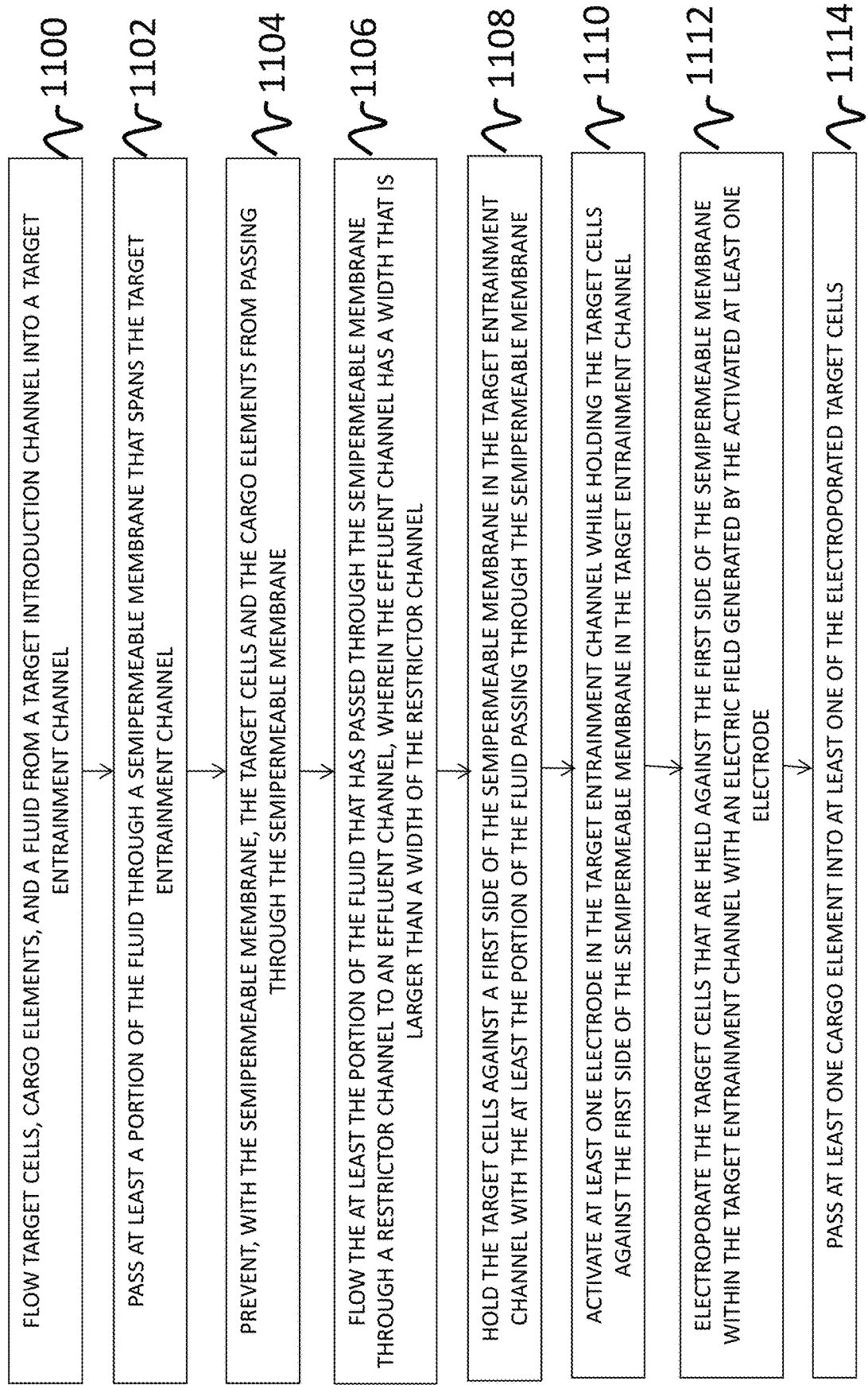
FIG. 11 illustrates a flow chart of illustrative operations that may be used for operating a microfluidic device in accordance with various aspects of the subject disclosure.

FIG. 11 depicts a flow chart of an example process for operation of a microfluidic device in accordance with various aspects of the subject technology. For explanatory purposes, the example process of FIG. 11 is described herein with reference to the components of FIGS. 1-10. Further for explanatory purposes, the blocks of the example process of FIG. 11 are described herein as occurring in series, or linearly. However, multiple blocks of the example process of FIG. 11 may occur in parallel. In addition, the blocks of the example process of FIG. 11 need not be performed in the order shown and/or one or more of the blocks of the example process of FIG. 11 need not be performed.

In the depicted example flow diagram, at block 1100, controller 104 may operate one or more pumps such as pumps 120 and 126 and/or one or more valves such as valves 132 and 138 to flow target cells 300, cargo elements 330, and a fluid from a target introduction channel 200 (e.g., in a first layer 114 of a microfluidic device 102/102' or in the target entrainment layer) into a target entrainment channel 202 (e.g., in a second layer 116 of the microfluidic device). The first layer 114 may be a separate substrate that is attached to a first side of the second layer 116 or can be formed in a common substrate with the target entrainment channel.

At block 1102, the controller may operate the pumps and/or valves to pass at least a portion of the fluid through a semipermeable membrane 117 (e.g., having a first side that is attached to an opposing second side of the second layer 116) that spans the target entrainment channel 202. The target cells and the cargo elements may flow into the target entrainment channel in the fluid together, or the target cells may flow into the target entrainment channel before or after flowing the cargo elements into the target entrainment channel.

At block 1104, the permeable membrane 117 prevents the target cells 300 and cargo elements 330 from passing through the semipermeable membrane (e.g., while at least the portion of the fluid flows through the membrane 117).

At block 1106, the controller may operate the pumps and/or valves to flow the at least the portion of the fluid that has passed through the semipermeable membrane 117 through a restrictor channel 204 (e.g., in a third layer 118 of the microfluidic device) to an effluent channel 206 (e.g., in the third layer). The third layer 118 may be attached to an opposing second side of the semipermeable membrane 117. The effluent channel 118 has a width $W_{EF}$ that is larger than a width $W_R$ of the restrictor channel 204. The target cells that are held against the first side of the semipermeable membrane in the target entrainment channel are encouraged or moved away from sidewalls of the target entrainment channel and toward a center of the target entrainment channel using the flow of the at least the portion of the fluid that has passed through the semipermeable membrane through the restrictor channel in the third layer of the microfluidic device to the effluent channel in the third layer.

At block 1108, the at least the portion of the fluid passing through the semipermeable membrane holds the target cells against the first side of the semipermeable membrane in the target entrainment channel.

At block 1110, at least one electrode 212 in the target entrainment channel 202 may be activated by the controller while holding the target cells against the first side of the semipermeable membrane 117 in the target entrainment channel 202. In this way, the target cells that are held against the first side of the semipermeable membrane within the target entrainment channel are electroporated with an electric field generated by the activated at least one electrode (block 1112).

At block 1114, while the target cells are held against the semipermeable membrane 117 and the electric field is present in the target entrainment channel, one or more one cargo elements 330 passes into at least one of the electroporated target cells to form transfected cells. The at least one electrode may then be deactivated, and the fluid including the at least one of the target cells having the at least one cargo element therein (e.g., the transfected cell) may flow along the first side of the semipermeable membrane 117 from the target entrainment channel 202 to a target collection reservoir 136.

Flowing the fluid including the at least one of the target cells having the at least one cargo element therein along the first side of the semipermeable membrane from the target entrainment channel to a target collection reservoir may include (see, e.g., FIGS. 2-4) flowing additional fluid from the target introduction channel to the target entrainment channel or may include (see, e.g., FIGS. 7-9) flowing additional fluid from the effluent channel through the restrictor channel and through the semipermeable membrane in a direction that is opposite to a direction of fluid flow for holding the target cells against the first side of the semipermeable membrane (as examples).

FIGS. 12A-12D illustrate experimental data demonstrating insertion of a small molecule, propidium iodide, into a primary human T cell's cytoplasm using a microfluidic device as described herein. Propidium Iodide (PI) is a small molecule that intercalates DNA, and fluoresces brightly red when bound. PI 1201 is added to the cell suspension, and enters the cells only if their membranes are permeabilized, e.g., by electroporation. As indicated in FIG. 12A, primary human T cells were labeled with calcein AM green to form calcein 1001 in the target cells, and then electroporated in the presence of PI. As shown in FIG. 12B, five 20-Volt, 200-microsecond pulses 1200 were applied, and the current through the channel was measured in order to characterize the cells' electric field exposure. FIG. 12B illustrates the measured current as a function of time. As indicated in FIG. 12A, electroporation pulses 1200 permeabilize the membranes of target cells with calcein 1001 and the PI cargo elements enter into the cells through the permeabilized membranes to form electroporated cargo-carrying cells 333'. Following the pulses, the cell membrane is no longer permeable to the PI as indicated by cargo-carrying cell 333 in FIG. 12A.

FIG. 12C shows before (1202) and after (1203) images of a portion of entrainment channel 202, respectively before and after electroporation pulses 1200 in which it can be seen that the green fluorescence of the calcein is replaced in image 1203 with red fluorescence from the PI cargo in the target cells. In this way, it was experimentally verified that the microfluidic devices 102 as disclosed herein caused electroporation of target cells as desired. FIG. 12D shows experimental data indicating that the PI signal started to increase concomitant with loss of calcein signal, indicating that the cell membrane had become permeabilized. In FIG. 12D, the calcein signal is shown by falling curve 1204, and the PI signal is shown by rising curve 1206.

Conventional electroporation methods often result in low cell viability due to heat generation (especially with primary cells). Furthermore, conventional electroporation is much less effective for DNA insertion (when compared to RNA insertion), because the material must cross two phospholipid bilayer membranes (the cell membrane and the nuclear membrane).

The systems and methods disclosed herein provide an improved approach to electroporation, which has advantages over the use of viral vectors for transfection, including adaptability to many cell types, higher speed, and higher safety. The systems and methods disclosed herein differ from other electroporation systems and methods in that they use flow against a membrane to temporarily immobilize cells at a particular location within the applied electric field, while the fluid flow simultaneously convectively transports heat out of the system. This combines the advantages of scale proffered by bulk electroporation with the precision of microscale electroporation. The geometry of the channels through which the fluid flows, further urges immobilized cells into the center of an entrainment channel for precision control of the location of the target cells.

Viral transduction is typically slower (e.g., hours instead of seconds) than electroporation, can only be used to shuttle DNA of limited size into cells, has issues with biosafety and mutagenesis, and is complicated, expensive, and time consuming (the virus with the desired payload must be created first). The performance of viral vectors is also highly dependent on cell type, and may not work for all of the targets mentioned in this disclosure. Mechanical transformation methods are complicated and expensive, inefficient, and process targets with low throughput. Variations in target size within a population render mechanical transformation methods very difficult to scale up and control.

While this specification contains many specific implementation details, these should not be construed as limitations on the scope of any inventions or of what may be claimed, but rather as descriptions of features specific to particular implementations of particular inventions. Certain features that are described in this specification, in the context of separate implementations, can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described components and systems can generally be integrated together in a single product or packaged into multiple products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements. Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A microfluidic device, comprising:
    a first substrate having a first side, an opposing second side, and a first channel;
    an electrode operable to generate an electric field in the first channel; and
    a semipermeable membrane having a first side that is attached to the opposing second side of the first substrate and that spans the first channel; and
    a second substrate attached to an opposing second side of the semipermeable membrane and having a second channel adjacent the semipermeable membrane and a third channel fluidly coupled to the second channel, wherein the first channel, the second channel, and the third channel each have an elongate dimension parallel to the semipermeable membrane, and wherein the third channel is relatively wider than the second channel in a direction parallel to the semipermeable membrane and perpendicular to the elongate dimensions of the first, second, and third channel,
    wherein the first channel comprises a target entrainment channel, and
    the first, second, and third channels are configured to, in the presence of a fluid flow from the first channel through the semipermeable membrane into the second and third channels, entrain a plurality of cells against the semipermeable membrane along the elongate dimension of the first channel away from the walls of the entrainment channel.

2. The microfluidic device of claim 1, further comprising:
    a first outlet port fluidly coupled between the first channel on the first side of the semipermeable membrane and a first collection reservoir; and
    a second outlet port fluidly coupled between the third channel in the second substrate and a second collection reservoir.

3. The microfluidic device of claim 1, wherein the electrode is disposed on a first sidewall of the first channel and wherein the microfluidic device further comprises an additional electrode disposed on an opposing second sidewall of the first channel.

4. The microfluidic device of claim 1, further comprising a target introduction channel configured for introduction of target cells and cargo elements into the first channel.

5. The microfluidic device of claim 4, wherein the target introduction channel is formed in a third substrate that is attached to the first side of the first substrate.

6. The microfluidic device of claim 5, wherein the target introduction channel has an elongate dimension that is not parallel to the elongate dimension of the first channel.

7. The microfluidic device of claim 1, wherein the microfluidic device comprises a unit device formed in a common package with a plurality of other microfluidic devices, each having a first channel in the first substrate, and second and third channels in the second substrate.

8. The microfluidic device of claim 7, further comprising a manifold substrate, the manifold substrate having an input port coupled, via a plurality of manifold channels, to the first channels of the microfluidic device and the plurality of other microfluidic devices.

9. The microfluidic device of claim 7, wherein the microfluidic device and the plurality of other microfluidic devices are linearly separated from each other within the common package.

10. The microfluidic device of claim 7, wherein the microfluidic device and the plurality of other microfluidic devices are angularly separated from each other about a common axis within the common package.

11. The microfluidic device of claim 1, wherein the second channel comprises a restrictor channel.

12. The microfluidic device of claim 11, wherein at least a portion of the restrictor channel is narrower than the first channel.

\* \* \* \* \*